United States Patent
Magna et al.

(10) Patent No.: US 7,223,374 B2
(45) Date of Patent: May 29, 2007

(54) HYDROFORMYLATION PROCESS EMPLOYING A COBALT-BASED CATALYST IN A NON-AQUEOUS LIQUID WITH IMPROVED CATALYST RECYCLING

(75) Inventors: Lionel Magna, Rueil Malmaison (FR); Hélène Olivier-Bourbigou, Rueil Malmaison (FR); Lucien Saussine, Croissy sur Seine (FR); Virginie Kruger-Tissot, Malakoff (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 11/350,881

(22) Filed: Feb. 10, 2006

(65) Prior Publication Data

US 2006/0128999 A1    Jun. 15, 2006

Related U.S. Application Data

(62) Division of application No. 10/411,389, filed on Apr. 11, 2003, now Pat. No. 7,060,860.

(30) Foreign Application Priority Data

Apr. 11, 2002 (FR) .................................. 02 04563

(51) Int. Cl.
*B01J 19/00* (2006.01)
*B01J 8/08* (2006.01)

(52) U.S. Cl. ...................... 422/224; 422/234; 422/261; 568/451; 568/454

(58) Field of Classification Search ................ 422/224, 422/234, 261, 242; 568/451, 454
See application file for complete search history.

(56) References Cited

U.S. PATENT DOCUMENTS 3,565,823 A    2/1971    Parshall (Continued)

FOREIGN PATENT DOCUMENTS

EP    11 065 95 A1    6/2001

(Continued)

OTHER PUBLICATIONS

XP-002223564—Organometallics 2000, vol. 19, pp. 3818-3823, "Ionic Phosphine Ligands with Cobaltocenium Backbone: Novel Ligands for the Highly Selective, Biphasic, Rhodium-Catalyzed Hydroformylation of 1-Octene in Ionic Liquids", Claudia C. Brasse et al.

(Continued)

*Primary Examiner*—N. Bhat
(74) *Attorney, Agent, or Firm*—Millen, White, Zelano & Branigan, P.C.

(57) ABSTRACT

A process for hydroformylating olefinically unsaturated compounds by means of a cobalt-based catalyst is carried out in a non-aqueous ionic liquid which is a liquid at a temperature below 90° C. and comprises at least one ammonium and/or phosphonium and/or sulfonium cation $Q^+$ and at least one anion $A^-$; catalyst recycling is improved by using a ligand selected from the group consisting of Lewis bases and employing a depressurization step between the pressurized reaction step and the step for separating the phases by decanting. At the end of said depressurization step, the organic phase is separated in the decanting step and the non-aqueous ionic liquid containing the catalyst can be re-used.

8 Claims, 1 Drawing Sheet

U.S. PATENT DOCUMENTS

| | | | | |
|---|---|---|---|---|
| 4,258,215 A | * | 3/1981 | Dawes | 568/454 |
| 4,567,305 A | * | 1/1986 | Matsumoto et al. | 568/454 |
| 5,763,679 A | * | 6/1998 | Nicholson et al. | 568/454 |
| 5,874,638 A | | 2/1999 | Chauvin et al. | |
| 5,919,987 A | * | 7/1999 | Kneuper et al. | 568/451 |
| 6,040,483 A | | 3/2000 | Olivier et al. | |
| 6,410,799 B1 | | 6/2002 | Favre et al. | |
| 6,469,216 B2 | * | 10/2002 | Hillebrand et al. | 568/454 |
| 6,617,474 B2 | | 9/2003 | Favre et al. | |
| 6,677,268 B2 | | 1/2004 | Hillebrand et al. | |

FOREIGN PATENT DOCUMENTS

| | | |
|---|---|---|
| EP | 11 821 87 A1 | 2/2002 |
| FR | 01 00970 | 7/2002 |

OTHER PUBLICATIONS

English translation of French Application No. 01.00970.

* cited by examiner

_US 7,223,374 B2_

HYDROFORMYLATION PROCESS EMPLOYING A COBALT-BASED CATALYST IN A NON-AQUEOUS LIQUID WITH IMPROVED CATALYST RECYCLING

This Application is A Divisional Of U.S. Ser. No. 10/411,389, Filed Apr. 11, 2003 now U.S. Pat. No. 7,060,860.

FIELD OF THE INVENTION

The present invention relates to a process for hydroformylating olefinically unsaturated compounds using a cobalt-based catalyst carried out in a two-phase medium, with improved catalyst recycling. One of the phases comprises a non-aqueous ionic liquid comprising at least one quaternary ammonium and/or phosphonium and/or sulfonium cation $Q^+$ and at least one anion $A^-$. The catalyst comprises at least one cobalt complex.

BACKGROUND OF THE INVENTION

Hydroformylating olefinic compounds is a reaction of great industrial importance and the majority of processes employ homogeneous catalysts dissolved in an organic phase comprising the reagents, products and possibly an excess of ligand, and so problems arise when separating and recovering the catalyst, in particular when the catalyst is used in relatively large quantities, as is the case with cobalt-based catalysts.

One solution to the problem has been mentioned by Bartik et al.: Organometallics (1993) 12, 164–170, J Organometal Chem (1994), 480, 15–21, and by Beller et al.: J Molecular Catal A: Chemical (1999), 143, 31–39. It consists of carrying out hydroformylation in the presence of an aqueous solution containing a cobalt complex which is rendered water-soluble by the presence of a phosphine-sulfonate ligand such as the sodium salt of trisulfonated triphenylphosphine or a trisulfonated tris(alkylphenyl)phosphine. International patent application WO-A-97/00132 describes cobalt clusters substituted by trialkoxysilylmethyl groups which renders them water-soluble. In that manner, the organic phase containing the aldehydes is readily separated from the aqueous phase containing the catalyst.

Despite the major industrial importance of said techniques for hydroformylating olefinic compounds, said two-phase systems suffer from a lack of solubility of the olefins in water, which results in relatively low reaction rates and makes them inapplicable to long chain olefins.

Further, U.S. Pat. No. 3,565,823 describes a technique consisting of dispersing a transition metal compound in a tin or germanium salt of a quaternary ammonium or phosphonium compound, with formula $(R^1R^2R^3R^4Z)YX_3$ in which $R^1$, $R^2$, $R^3$ and $R^4$ are hydrocarbyl groups containing up to 18 carbon atoms, Z is nitrogen or phosphorus, Y is tin or germanium and X is a halogen, either chlorine or bromine. U.S. Pat. No. 3,832,391 describes a process for carbonylating olefins using the same composition. Those compositions suffer from the disadvantage of having a relatively high melting point, for example over 90° C., which complicates manipulation of the solutions of catalyst and reaction products.

U.S. Pat. No. 5,874,638, commonly assigned, describes benefiting both from employing two phases while avoiding the drawbacks due to using water, and from the use of compounds with high melting points by dissolving certain catalytic compounds of transition metals from groups 8, 9 and 10, known to catalyse hydroformylation, in non-aqueous ionic liquids constituted by organic-inorganic salts that are liquid at ambient temperatures. However, when the catalyst comprises a salt or a cobalt complex, it is very difficult to prevent at least partial formation of dicobalt-octacarbonyl and/or cobalt-tetracarbonyl hydride under the hydroformylation reaction conditions. These two compounds are highly soluble in the organic reaction phase constituted by at least the olefinic reagent and the aldehydes produced, and so recycling the cobalt using the non-aqueous ionic liquid phase is only partial, causing loss of catalyst.

SUMMARY OF THE INVENTION

It has now been discovered that in the hydroformylation reaction catalysed by cobalt complexes employed in a non-aqueous ionic liquid comprising at least one ammonium and/or phosphonium and/or sulfonium cation $Q^+$ and at least one anion $A^-$ which is liquid at a temperature of less than 90° C., recycling the metal in the ionic liquid is greatly improved by using a ligand selected from the group consisting of Lewis bases and using an intermediate depressurization step between the pressurized reaction step and the step for separating the phases by decanting. At the end of this depressurization step, the organic phase is separated in the decanting step and the non-aqueous ionic liquid phase containing the catalyst can be re-used.

More precisely, the invention provides a process for liquid phase hydroformylation of olefinically unsaturated compounds, comprising a pressurized reaction step carried out in the presence of at least one non-aqueous ionic liquid comprising at least one salt with general formula $Q^+ A^-$ in which $Q^+$ represents a quaternary ammonium cation and/or a quaternary phosphonium cation and/or a quaternary sulfonium cation and $A^-$ represents an anion, and a step for decanting the final products, said process being characterized in that the catalyst comprises at least one complex of cobalt with at least one ligand selected from the group consisting of Lewis bases and in that an intermediate depressurization step is carried out between the reaction step and the decanting step.

Without wishing to be bound by any particular theory, under the conditions of the hydroformylation reaction pressurized with synthesis gas, most of the catalyst can be considered to be present in the form of the complexes $Co_2(CO)_8$, $Co_2(CO)_6L_2$, $HCo(CO)_4$ and $HCo(CO)_3L$ in which L is the Lewis base ligand, and in the step for depressurization prior to phase separation, the presence of the basic ligand L encourages the formation of ionic cobalt complexes such as $(CoL_6)^{++}[Co(CO)_4^-]_2$ which have a high affinity for the phase containing the non-aqueous ionic liquid.

The non-aqueous ionic liquid is selected from the group consisting of liquid salts with general formula $Q^+ A^-$ in which $Q^+$ represents a quaternary ammonium and/or a quaternary phosphonium and/or quaternary sulfonium cation and $A^-$ represents any anion that is capable of forming a liquid salt at low temperatures, i.e., below 90° C. and advantageously at most 85° C., and preferably below 50° C. Preferred anions $A^-$ are nitrate, sulfate, phosphate, acetate, halogenoacetates, tetrafluoroborate, tetrachloroborate, tetraalkylborates, tetraarylborates, hexafluorophosphate, hexafluoroantimonate, fluorosulfonate ions, alkylsulfonates, perfluoroalkylsulfonates, bis(perfluoroalkylsulfonyl)amides and arenesulfonates, the latter optionally being substituted with halogen or halogenoalkyl groups.

The quaternary ammonium and/or phosphonium cation(s) $Q^+$ preferably has/have general formulae $NR^1R^2R^3R^{4+}$ and PR$^1$R$^2$R$^3$R$^{4+}$, or general formulae R$^1$R$^2$N=CR$^3$R$^{4+}$ in which R$^1$, R$^2$, R$^3$ and R$^4$, which may be identical or different, represent hydrogen (with the exception of the cation NH$_4^+$ for NR$^1$R$^2$R$^3$R$^{4+}$); preferably, a single substituent represents hydrogen, or hydrocarbyl groups containing 1 to 30 carbon atoms, for example alkyl groups that may or may not be saturated, cycloalkyl or aromatic groups, or aryl or aralkyl groups that may be substituted, containing 1 to 30 carbon atoms. The ammonium and/or phosphonium cations can also be derived from nitrogen-containing and/or phosphorus-containing heterocycles containing 1, 2 or 3 nitrogen and/or phosphorus atoms in which the cycles are constituted by 4 to 10 atoms, preferably 5 or 6 atoms.

The quaternary ammonium and phosphonium cations may also satisfy the following formulae respectively:

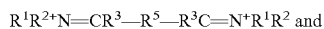

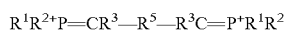

in which R$^1$, R$^2$ and R$^3$, which may be identical or different, are as defined above, and R$^5$ represents an alkylene or phenylene radical. Among groups R$^1$, R$^2$, R$^3$ and R$^4$, the radicals may be methyl, ethyl, propyl, isopropyl, butyl, secondary butyl, tertiary butyl, amyl, methylene, ethylidene, phenyl or benzyl; R$^5$ may be a methylene, ethylene, propylene or phenylene group.

The ammonium and/or phosphonium cation Q$^+$ is preferably selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, diethylpyrazolium, N-butyl-N-methylpyrrolidinium, trimethylphenylammonium, tetrabutyl-phosphonium and tributyl-tetradecylphosphonium.

The sulfonium cations for use in the invention can have general formula SR$^1$R$^2$R$^{3+}$, where R$^1$, R$^2$ and R$^3$, which may be identical or different, each represent a hydrocarbyl radical containing 1 to 12 carbon atoms, for example an alkyl, saturated or unsaturated, cycloalkyl or aromatic, aryl, alkaryl or aralkyl group containing 1 to 12 carbon atoms.

Examples of salts that can be for use in the invention that can be cited are N-butylpyridinium hexafluorophosphate, N-ethyl pyridinium tetrafluoroborate, pyridinium fluorosulfonate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methylimidazolium trifluoroacetate, 3-butyl-1-methylimidazolium trifluoromethylsulfonate, 3-butyl-1-methylimidazolium bis(trifluoromethylsulfonyl)amide, trimethylphenylammonium hexafluorophosphate and tetrabutylphosphonium tetrafluoroborate. These salts may be used alone or as a mixture.

The catalyst cobalt compound precursors are selected from the group consisting of cobalt salts such as acetylacetonates, carboxylates and in particular the formate or acetate, and carbonyl complexes such as dicobalt-octacarbonyl, cobalt-tetracarbonyl hydride and carbonyl clusters. The choice of cobalt precursor compound is not critical but preferably, halides are generally avoided.

The basic Lewis ligand is selected from the group consisting of oxygen-containing ligands, sulfur-containing ligands, nitrogen-containing ligands and phosphorus-containing ligands, which may or may not be substituted by ionic functional groups such as sulfonates, carboxylates, phosphates, ammonium and phosphonium compounds.

More particularly, the oxygen-containing ligands are selected from the group consisting of alcohols, phenols, ethers, ketones and acetals. Non-limiting examples that can be cited are methanol, ethanol, phenol, diethylether, dibutylether, diphenylether, tetrahydrofuran, 1,4-dioxane, 1,3-dioxolane, glyme, diglyme, acetone, methylethylketone, acetophenone, methylal, 2,2-dimethoxypropane and 2,2-di (2-ethylhexyloxy)-propane.

More particularly, the sulfur-containing ligands are selected from the group consisting of thiols, thiophenols, thioethers and disulfides. Non-limiting examples that can be cited are methanethiol, ethanethiol, thiophenol, diethylsulfide, dimethyldisulfide and tetrahydrothiophene.

More particularly again, the nitrogen-containing ligands are selected from the group consisting of monoamines, di-, tri- and poly-amines, imines, diimines, pyridines, bipyridines, imidazoles, pyrroles and pyrazoles. Non-limiting examples that can be cited are methylamine, trimethylamine, triethylamine, ethylenediamine, diethylenetriamine, diazabicyclooctane, N,N'-dimethylethane-1,2-diimine, N,N'-di-t-butylethane-1,2-diimine, N,N'-di-t-butylbutane-2,3-diimine, N,N'-diphenylethane-1,2-diimine, N,N'-bis-(2,6-dimethylphenyl)ethane-1,2-diimine, N,N'-bis-(2,6-diisopropylphenyl)ethane-1,2-diimine, N,N'-diphenylbutane-2,3-diimine, N,N'-bis-(2,6-dimethylphenyl)butane-2,3-diimine, N,N'-bis-(2,6-diisopropylphenyl)butane-2,3-diimine, pyridine, 2-picoline, 4-picoline, t-butyl-2-pyridine, di-(t-butyl)-2,6-pyridine, 2,2'-bipyridine, imidazole, N-methylimidazole, N-butylimidazole, pyrrole, N-methylpyrrole and 2,5-dimethylpyrrole.

More particularly, the phosphorus-containing ligands are selected from the group consisting of phosphines, polyphosphines, phosphine oxides and phosphites. Non-limiting examples that can be cited are tributylphosphine, triisopropylphosphine, tricyclohexylphosphine, triphenylphosphine, tris(o-tolyl) phosphine, bis(diphenylphosphino)ethane, trioctylphosphine oxide, triphenylphosphine oxide and triphenylphosphite.

Preferred ligands are selected from the group consisting of pyridines and phosphines substituted with ionic functional groups such as sulfonates, carboxylates, phosphates, ammonium or phosphonium compounds. Non-limiting examples that can be cited are:

1-(4-pyridyl)-2-(dicyclopentylmethylphosphonium)-ethane tetrafluoroborate: ligand (1);

1-(N-imidazolyl)-2-(dicyclopentylmethylphosphonium)-ethane tetrafluoroborate: ligand (2);

1-(diphenylphosphino)-2-(4-N-methylpyridinium)-ethane tetrafluorophosphate: ligand (3);

1-(dicyclopentylphosphino)-2-(3-methylimidazolium-1-yl)-ethane hexafluorophosphate: ligand (4);

the tetrabutyl ammonium triphenylphosphine trisulfonate ligand;

the sodium triphenylphosphine trisulfonate ligand (or TPPTS);

the sodium triphenylphosphine monosulfonate ligand (or TPPMS);

(3-methylimidazolium-1-yl hexafluorophosphate)-2-pyridine: ligand (5); and bis(3-methylimidazolium-1-yl hexafluorophosphate)-2,6-pyridine: ligand (6).

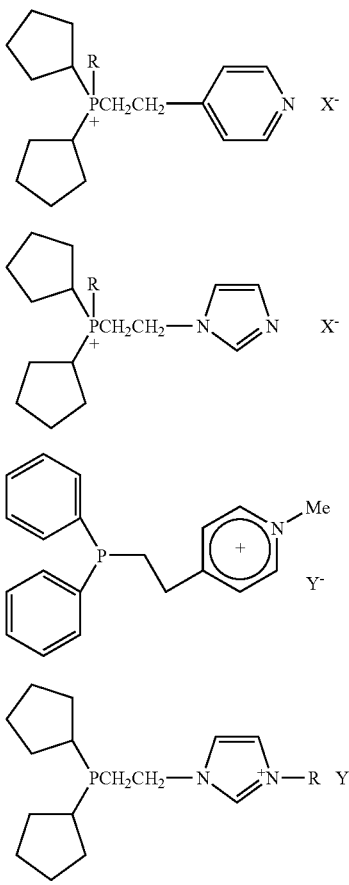

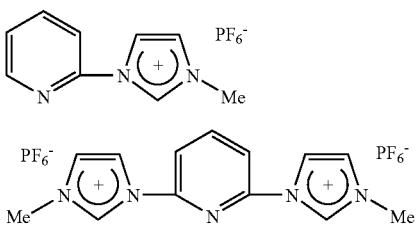

The catalytic composition is obtained by mixing the ionic liquid with the cobalt compound and the ligand, in any manner. It is also possible to dissolve the transition metal compound and/or ligand in an organic solvent in advance.

The complex between the cobalt precursor and the ligand can be prepared in advance of the reaction by mixing the cobalt precursor with the ligand in a suitable solvent, for example an organic solvent or the non-aqueous ionic liquid that will then be used in the catalytic reaction. The complex can also be prepared in situ by mixing the cobalt precursor and the ligand directly in the hydroformylation reactor. It is also possible to inject the ligand only at the depressurization step following reaction.

The concentration of the cobalt complex in the non-aqueous ionic liquid is not critical. It is advantageously in the range 0.1 mmoles per liter of ionic liquid to 5 moles per liter, preferably in the range 1 mmole to 1 mole per liter, and more preferably between 10 and 500 mmoles per liter. The mole ratio between the ligand and the cobalt compound is in the range 0.1:1 to 500:1, preferably in the range 1:1 to 100:1.

Olefinically unsaturated compounds that can be hydroformylated are selected from the group consisting of mono-olefins, di-olefins, in particular conjugated di-olefins, and olefinic compounds comprising one or more heteroatoms, in particular from unsaturated groups such as the ketone or carboxylic acid function. Non-limiting examples that can be cited are the hydroformylation of pentenes to hexanal and methylpentanal, hexenes to heptanals and isoheptanals, isooctenes to isononanals, isodecenes to iso-undecanals, and olefinic $C_{11}$ to $C_{16}$ cuts to $C_{12}$ to $C_{17}$ aldehydes. Said olefinic compounds can be used in the pure form or diluted with saturated or unsaturated hydrocarbons.

The ratio of the partial pressures of the hydrogen to carbon monoxide used in the reaction medium for hydroformylation can be 10:1 to 1:10, preferably in a ratio of 1:1, but any other ratio can be used when carrying out the process.

The temperature at which hydroformylation is carried out is in the range 30° C. to 200° C.; advantageously the temperature is below 180° C., preferably in the range 50° C. to 150° C. The pressure can be in the range 1 MPa to 20 MPa, preferably in the range 2 MPa to 15 MPa. Examples of particular conditions are a temperature of 95° C. and a pressure of 6.5 MPa or a temperature of 140° C. and a pressure of 10 MPa.

The reaction for the catalytic hydroformylation of unsaturated compounds can be carried out in a closed, a semi-open or a continuous system with one or more reaction stages. In a continuous implementation, the effluent from the pressurized reactor is transferred into a vessel in which it is depressurized to a pressure of less than 1 MPa and preferably to atmospheric pressure, to a temperature of at most 150° C. and preferably below 60° C. Contact between the two liquid phases can be maintained in this step by mechanical stirring or by any other suitable means for example, by vigorous pumping using cocurrent or countercurrent circulation known as "pump around" or by suction and redispersion of droplets by, for example, an "Ultraturax®" device. The function of the stirring is to provide sufficient area for mass transfer by breaking up the phases into droplets. Stirring during depressurization is not mandatory but is preferred. Minimum depressurization times depends particularly on the initial pressure, the size of the vessel, the volatility of the products and the power of the stirring (if any during this step). In any case, the depressurization is conducted sufficiently slowly and in combination with sufficient mixing of the phases, if employed, to transfer at least 50% (preferably at least 90%, more preferably at least 99%) of the cobalt complex from the organic phase to the non-aqueous ionic liquid phase. Accordingly, the contact time in the depressurization vessel should be sufficient to ensure optimal transfer of the catalyst to the non-aqueous ionic liquid phase.

At the outlet from the depressurization vessel, the organic phase containing the reaction products is advantageously separated simply by decanting the non-aqueous ionic liquid phase containing almost all of the catalyst. At least a portion of this ionic liquid phase, which contains the catalyst, is returned to the reactor; the other portion can be processed to eliminate catalyst decomposition residues.

The invention also relates to apparatus for carrying out the hydroformylation process as defined in the above description, said apparatus comprising:

at least one reactor A1;

at least one depressurization vessel ("depressurizer") B1;

at least one decanter B2 to decant the polar phase containing at least the non-aqueous ionic solvent containing at least the catalyst which is recycled to reactor A1;

and also:

at least one line 1 for introducing feed to be hydroformylated and the carbon monoxide/hydrogen mixture;

at least one line 2 for transferring the effluent from the reactor to the depressurizer B1;

at least one line 3 for sending the mixture of the organic effluent and the ionic solvent contained in the depressurizer B1 to the decanter B2;

at least one line 6 for returning the gas from the depressurizer B1 to the reactor A1;

at least one line 5 for returning the polar phase containing at least the ionic liquid and the catalyst separated in B2 to the reactor A1;

at least one line 7 which can withdraw the as synthesized reaction products from the decanter B2.

The apparatus also comprises:

in the separation section, at least one column A2 for separating the crude reaction products from the unreacted olefinically unsaturated compound to be hydroformylated;

and also:

at least one line 4 for recycling the unreacted olefinically unsaturated compound to be hydroformylated separated in column A2 to the reactor A1;

at least one line 8 which can send the products leaving from the foot of the column A2 to the remainder of the product fractionation train.

BRIEF DESCRIPTION OF DRAWING

The process and apparatus of the invention will be better understood from the description below, made with reference to the attached drawing which is a schematic flowsheet.

DETAILED DESCRIPTION OF DRAWING

Figure 1:
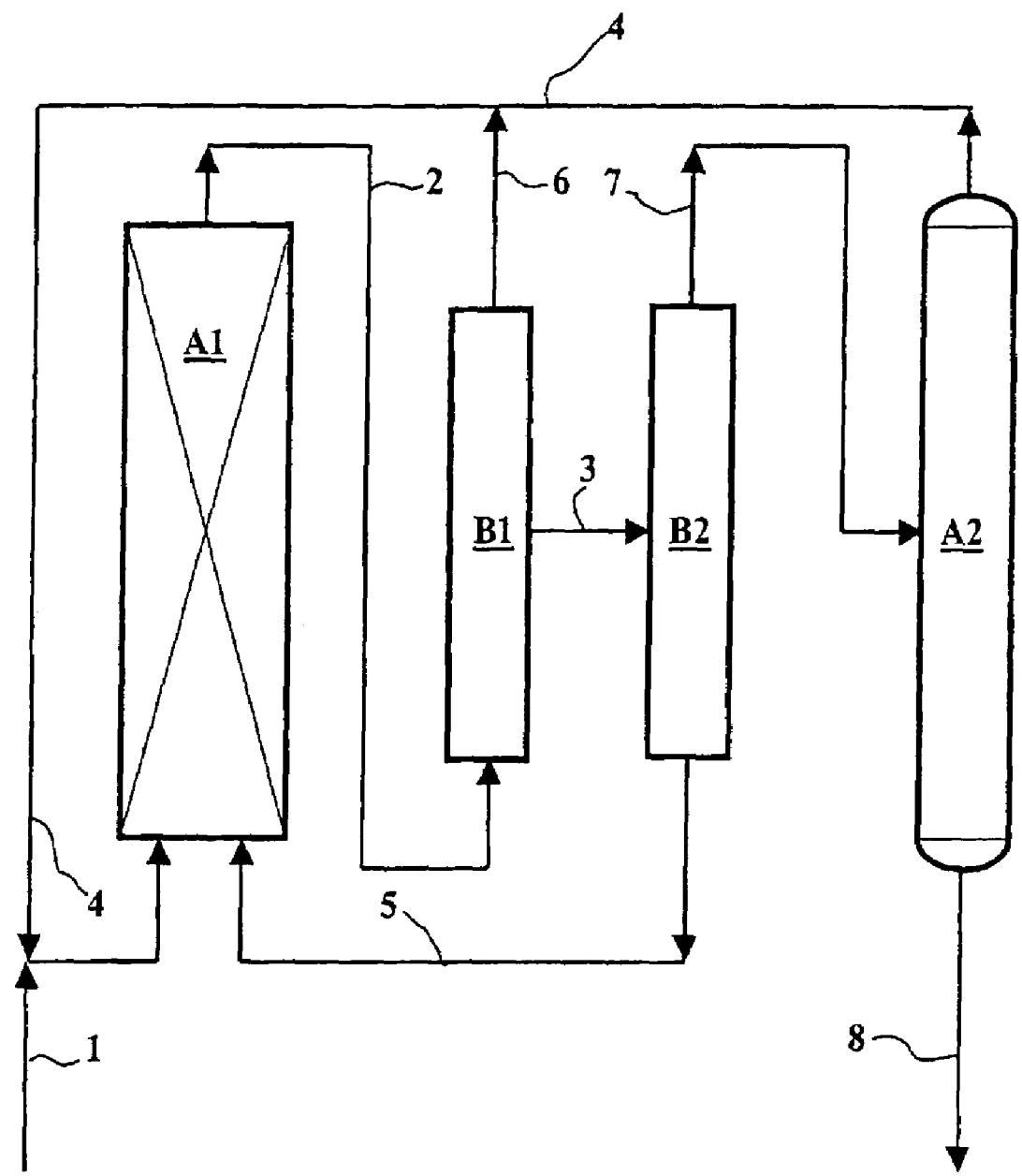

In the drawing, the reaction is carried out in the reactor A1 in the presence of the feed to be hydroformylated, which can be introduced via line 1, of a transition metal compound(s), of a Lewis base ligand (which can optionally be introduced as a mixture with the transition metal compound(s)), and of a carbon monoxide and hydrogen, which can be introduced via line 1, and in the presence of at least one non-aqueous ionic liquid. The ionic liquid can be introduced into the reactor at the start of the reaction. Optionally, fresh ionic liquid can be injected into the reactor A1 during the reaction and used ionic liquid can be withdrawn from A1 (the means for injecting and withdrawing the ionic ligand are not shown in the drawing).

The heat of reaction is removed by techniques that are known to the skilled person and which are not shown in the drawing.

At the outlet from the reaction section, the reactor effluent is sent via line 2 to at least one depressurizer B1 in which the pressure is reduced. Stirring can be maintained in B1 either by mechanical means or by any other suitable means. The gas released by the depressurization escapes via line 6 and is returned to the reactor A1 after recompression.

The effluent from depressurizer B1 is sent to decanter B2 via line 3. In decanter B2, the polar phase which contains at least the ionic liquid and the catalyst is separated from the product mixture and organic solvent is returned to the reactor A1 via line 5.

The organic phase separated out in decanter B2 is sent to a distillation column A2 via a line 7. In column A2, the unreacted olefinically unsaturated compound to be hydroformylated is separated overhead. It is recycled to reactor A1 via line 4. The crude reaction products collected from the bottom of A2 are sent via a line 8 to a specific fractionation train (not shown).

The following examples illustrate the invention without limiting its scope.

EXAMPLE 1

The hydroformylation reaction was carried out in a 300 ml stainless steel autoclave provided with a double jacket for regulating the temperature by circulation of a heat transfer fluid and provided with a conventional efficient mechanical paddle—counter-paddle stirring system generally operating at 250 to 2500 rpm, preferably 500 to 1000 rpm. 0.4 g of dicobalt-octacarbonyl (2.3 mmole of cobalt), 1 molar equivalent of deaerated and distilled pyridine (Lewis base ligand), 10 ml of 3-butyl-1-methylimidazolium bis(trifluoroethylsulfonyl) amide (non-aqueous ionic liquid), 30 ml of heptane and 30 ml of 1-hexene were introduced into the autoclave which had been purged of air and moisture and placed under 1 atmosphere of hydrogen-carbon monoxide (1:1 molar) synthesis gas. The pressure of the synthesis gas was raised to 10 MPa and the temperature was raised to 140° C. and stirring was commenced. After reacting for 3.5 hours, the synthesis gas inlet was closed and the reactor was allowed to cool to 25° C. Maintaining the stirring, the pressure was slowly released from 10 MPa to atmospheric pressure during a period of 30 minutes. Stirring was then stopped and the reaction mixture was allowed to decant overnight. After removal from the autoclave, the upper organic phase was slightly colored.

Gas chromatographic analysis of the two phases after flashing and weighing the non flashed residues produced the material balance of the reaction. The 1-hexene conversion yield was 99.5% by weight. The selectivity for $C_7$ aldehydes was 77.6% and the n/iso (n-heptanal/isoheptanals) ratio was 1.2. The organic phase contained 7.3% of the totality of cobalt engaged in the reaction.

EXAMPLE 2

The hydroformylation reaction was carried out in the same apparatus and using the same method as that described in Example 1 with the exception that the autoclave was degassed without stirring. After reacting for 4 hours, the autoclave was emptied. The upper organic phase was slightly colored.

The 1-hexene conversion yield was 97.9% by weight. The selectivity for $C_7$ aldehydes was 85.9% and the n/iso (n-heptanal/isoheptanals) ratio was 1.6. The cobalt metal content of the organic phase was 440 ppm (parts per million by weight), correspond to 12.8% of the cobalt engaged in the reaction.

EXAMPLE 3

The hydroformylation reaction was carried out in the same apparatus and using the same method as that described in Example 1 with the exception that the ligand was bis(3-methylimidazolium-1-yl hexafluorophosphate)-2,6-pyridine (1 molar equivalent with respect to cobalt) and the non-aqueous ionic liquid was 3-butyl-1-methylimidazolium hexafluorophosphate. After reacting for 3 hours, the autoclave was emptied. The upper organic phase was practically colorless.

The 1-hexene conversion yield was 97.7% by weight. The selectivity for $C_7$ aldehydes was 55.3% and the n/iso (n-heptanal/isoheptanals) ratio was 0.9. The cobalt metal content of the organic phase was 15 ppm (parts per million by weight), corresponding to 0.5% of the cobalt engaged in the reaction.

EXAMPLE 4

The hydroformylation reaction was carried out in the same apparatus and using the same method as that described in Example 1 with the exception that the ligand was sodium triphenylphosphine monosulfonate (1 molar equivalent with respect to cobalt). After reacting for 6 hours, the autoclave was emptied. The upper organic phase was slightly colored.

The 1-hexene conversion yield was 96.8% by weight. The selectivity for $C_7$ aldehydes was 73.7% and the n/iso (n-heptanal/isoheptanals) ratio was 1.4. The cobalt metal content of the organic phase was 180 ppm (parts per million by weight), corresponding to 6% of the cobalt engaged in the reaction.

EXAMPLE 5 (COMPARATIVE)

The hydroformylation reaction was carried out in the same apparatus and using the same method as that described in Example 1 with the exception that no ligand was introduced. After reacting for 6 hours, the autoclave was emptied. The upper organic phase was a strongly colored deep brown.

The 1-hexene conversion yield was 99.6% by weight. The selectivity for $C_7$ aldehydes was 18.5% and the n/iso (n-heptanal/isoheptanals) ratio was 0.4. The organic phase contained 90% of the cobalt engaged in the reaction.

This comparative example shows that in the absence of a ligand, recycling the cobalt in the non-aqueous ionic liquid is compromised by the solubility of the carbonyl complexes in the organic phase.

EXAMPLE 6 TO 10 (COMPARATIVE)

The same behavior characteristic of the absence of a ligand as shown in Example 5 was verified using a wide range of ionic liquids:
Example 6: 3-butyl-1-methylimidazolium tetrafluoroborate;
Example 7: 3-butyl-1-methylimidazolium bis(trifluoromethylsulfonyl) amide;
Example 8: 3-butyl-2-methyl-1-methylimidazolium hexafluorophosphate;
Example 9: 3-butyl-2-methyl-1-methylimidazolium tetrafluoroborate; and
Example 10: 3-butyl-2-methyl-1-methylimidazolium bis(trifluoromethylsulfonyl) amide.

In these examples carried out without ligands, for the same conversion and the same selectivity as that obtained in Example 5, quantities of cobalt metal in the organic phase were observed that corresponded to proportions of 70% to 100% of the cobalt engaged in the reaction.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application -02/04563, filed Apr. 11, 2002, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An apparatus for carrying out hydroformylation of olefinically unsaturated compounds, said apparatus comprising:
    at least one reactor, A1, for reacting at least one olefinically unsaturated compound with hydrogen and carbon monoxide to form a hydroformylation effluent in the presence of at least one non-aqueous ionic liquid, wherein said reactor includes means for putting the reactor contents under pressure and stirring the reactor contents, and wherein the reactor contains at least one catalyst comprising at least one complex of cobalt with at least one ligand selected from the group consisting of Lewis bases;
    at least one depressurization vessel, B1, separate from the reactor A1, for depressurizing the hydroformylation effluent sufficiently slowly to transfer at least 50% of the cobalt complex from the organic phase to the polar phase containing the non-aqueous ionic liquid phase; and
    at least one decanter, B2, for decanting the polar phase containing at least the non-aqueous ionic solvent containing at least the catalyst for recycling to reactor A1;
    the reactor, depressurization vessel and decanter being operatively connected with one another by:
    at least one line 1 for introducing said at least one olefinically unsaturated compound to be hydroformylated and a carbon monoxide/hydrogen mixture into reactor A1;
    at least one means for providing said at least one non-aqueous ionic liquid in said reactor A1,
    at least one line 2 for transferring the effluent from the reactor A1 to the depressurization vessel B1;
    at least one line 3 for sending the mixture of the organic effluent phase and the polar phase containing the non-aqueous ionic solvent from the depressurization vessel B1 to the decanter B2;
    at least one line 6 for returning the gas from the depressurization vessel B1 to the reactor A1;
    at least one line 5 for returning the polar phase containing at least the ionic liquid and the catalyst separated in decanter B2 to the reactor A1; and
    at least one line 7 for withdrawing the organic effluent phase containing synthesized reaction products from the decanter B2.

2. An apparatus according to claim 1 further comprising:
    in communication with the at least one line 7 for withdrawing the organic effluent phase containing synthesized reaction products from the decanter B2, at least one column A2 for separating the crude reaction products from unreacted olefinically unsaturated compound;
    at least one line 4 for recycling the unreacted olefinically unsaturated compound separated in column A2 to the reactor A1; and at least one line 8 for sending the products leaving from the foot of the column A2 to the remainder of a product fractionation train.

3. The apparatus of claim 1 wherein the depressurization vessel is for depressurizing the effluent from the hydroformylation reaction to a pressure of less than 1 MPa at a temperature of at most 150° C., and the depressurization vessel includes means for mechanical stirring to provide contact between the two liquid phases.

4. The apparatus of claim 1, wherein the depressurization vessel is for depressurizing the effluent from the hydroformylation reaction to atmospheric pressure.

5. The apparatus of claim 1, wherein the reactor is for carrying out the hydroformylation reaction at a temperature in the range 30° C. to 200° C., and at a pressure in the range 1 MPa to 20 MPa.

6. The apparatus of claim 1, wherein the at least one depressurization vessel, B1, is for depressurizing the hydroformylation effluent sufficiently slowly to transfer at least 90% of the cobalt complex from the organic effluent phase to the polar phase containing the non-aqueous ionic liquid.

7. The apparatus of claim 1, wherein the at least one depressurization vessel, B1, is for depressurizing the hydroformylation effluent sufficiently slowly to transfer at least 99% of the cobalt complex from the organic effluent phase to the polar phase containing the non-aqueous ionic liquid.

8. The apparatus of claim 1, wherein the depressurization vessel includes means for stirring the phases during depressurization.

* * * * *